US00PP12022P2

(12) United States Plant Patent

Butler, III

(10) Patent No.: US PP12,022 P2
(45) Date of Patent: Jul. 31, 2001

(54) *TRICHILIA DREGEANA* PLANT NAMED 'M1'

(76) Inventor: George C. Butler, III, 17905 SW. 216$^{th}$ St., Miami, FL (US) 33170

( * ) Notice: Subject to any disclaimer, the term of this patent is extended or adjusted under 35 U.S.C. 154(b) by 0 days.

(21) Appl. No.: 09/299,421

(22) Filed: Apr. 26, 1999

(51) Int. Cl.$^{7}$ ..... A01H 5/00
(52) U.S. Cl. ..... Plt./216
(58) Field of Search ..... Plt./226, 216

(56) References Cited

PUBLICATIONS http://www.wits.ac.za/museums/herbarium/treflis.htm, p. 16, Oct. 2000.* http://www.rbgkew.org.uk/dcgi–bin/web.dbs/genform.pl, Oct. 2000.* http://www.sntc.org.sz/checklst/malflch6.html, p. 1, Oct. 2000.*

* cited by examiner

*Primary Examiner*—Bruce R. Campell
*Assistant Examiner*—Wendy C Baker
(74) *Attorney, Agent, or Firm*—Christie, Parker & Hale, LLP

(57) ABSTRACT

A variety of *Trichilia dregeana* having small leaves and short internodal spacing.

1 Drawing Sheet

BACKGROUND OF THE INVENTION

The present invention relates to a new and distinct cultivar discovered as a natural mutation of an unnamed plant in a controlled planting of *Trichilia dregeana* (believed to be unpatented) in Dade County, Fla. The varietal denomination of the new cultivar is 'M1'.

The new variety has been asexually reproduced by rooted cuttings in Dade County, Fla. Asexual reproduction through succeeding generations has established that the combination of characteristics as herein disclosed for the new cultivar are firmly fixed and retained through successive generations of asexual reproduction. Various methods of asexual reproduction, such as micropropagation, layering and reproduction from vegetative cuttings, may be used to reproduce the new variety.

SUMMARY OF THE INVENTION

Among the distinguishing characteristics of the new variety are significantly smaller compound leaves with shorter internodal spacing than its parents.

BRIEF DESCRIPTION OF ILLUSTRATIONS

The accompanying color photographic illustration shows a typical specimen of the new variety in colors as nearly true as possible with an illustration of this type, in comparison with the parent.

DESCRIPTION OF THE NEW VARIETY

In the description herein, color references are to The Royal Horticultural Society Colour Chart (R.H.S.C.C.). The terminology used in the color descriptions herein refers to plate numbers in this color chart.

The following description is from plants grown in Dade County, Fla., during the months of June. Plants are 24 weeks old from seedling stage and grown in 2500 foot candles of light.

Plant:

*A. Form.*—Upright, compact. Size: About 4 feet with 2 foot spread 12 months from 2 inch cutting.

*B. Growth.*—Very vigorous, uniform branching habit.

*C. Foliage.*—Size: About 5 to 6 inches long; about 2 to 2½ inches wide. Quantity: About 9 leaflets per compound leaf on a 4 foot tall plant (see photo illustration for details). Leaf form: Leaves are pinnately compound. Leaflets are ovate in shape with an entire margin, an acute tip, and an attenuate to rounded base. Leaves and leaflets appear glabrous. Color New foliage: Upper side near 137A; underside near 137C. Old foliage: Upper side near 131A; underside near 137B. Texture: Upper side smooth; underside rough. Edge: Smooth and rippled. Serration: Not serrated. Petiole: Top surface near 137A Petioles average about 0.1 inch diameter at stipule about 0.25 inches at base; average stipule is about 2.5 times larger than petiole diameter; bark begins to form on base as well. Rachis: Slightly hairy, fuzzy. Variegation: None. Veination: Concave on top side of leaf; same color as surrounding tissue; lateral veins underneath are more pronounced and raised; color changes from 137B on tissue to 137C on veins. Wood New shoots: Near 137A. Bark: Smooth. Old wood: Near 177B. Bark: Smooth.

*Winter hardiness.*—Withstands 34° F.

*Resistance to disease.*—Similar to species.

*Characteristics.*—Temperature range: About 34° F. to 105° F. Internode spacing: About 1½ inches to 2 inches. Preferred growing conditions: Full sun to about 73% shade. Growth habit: Upright. Leaves per stem: First juvenile leaf compound 3, increasing to 7 leaflets on a 4 foot tall plant.

I claim:

1. A new and distinct variety of Trichilia substantially as illustrated and described.

* * * * *

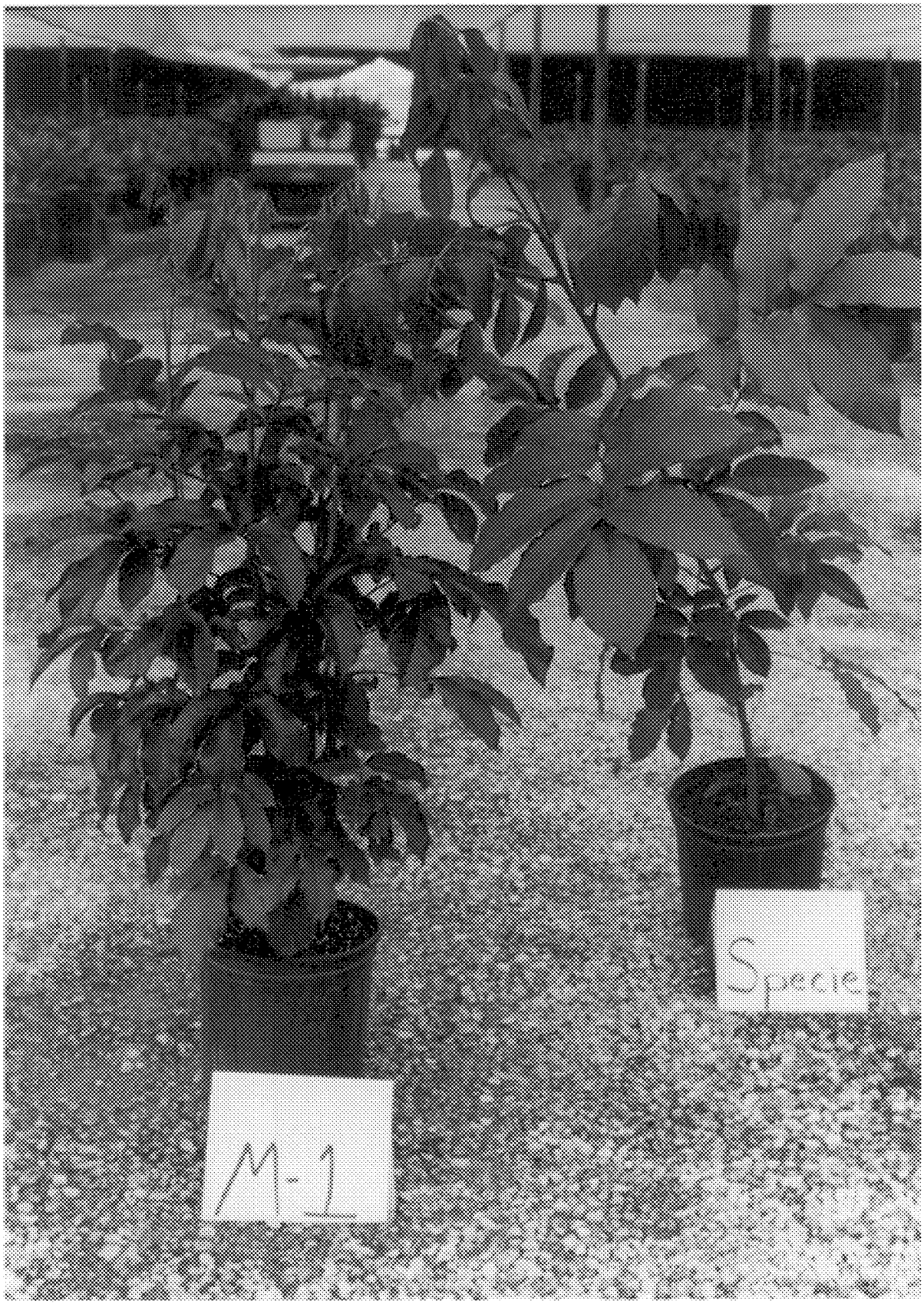
M-1
Spore